Dec. 17, 1974 C. G. KLEHM Plant Pat. 3,667
PEONY PLANT
Filed Oct. 24, 1973
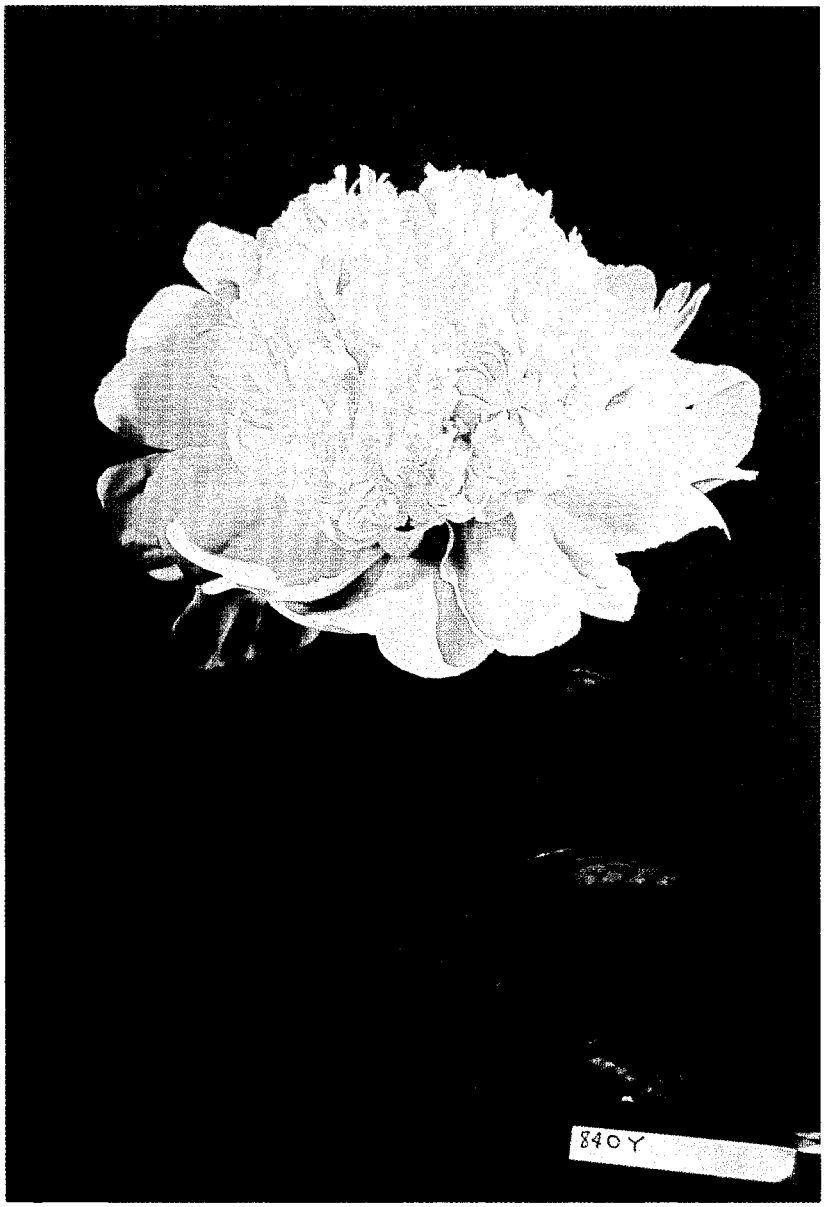

United States Patent Office

Plant Pat. 3,667
Patented Dec. 17, 1974

3,667
PEONY PLANT

Carl George Klehm, Arlington Heights, Ill., assignor to Klehm Properties, Inc., Arlington Heights, Ill.

Filed Oct. 24, 1973, Ser. No. 409,171
Int. Cl. A01h *5/00*
U.S. Cl. Plt.—68 1 Claim

ABSTRACT OF THE DISCLOSURE

A new variety of Paeonia Lactiflora characterized by its profuse production of bomb shaped flowers having a unique coloration comprising a blend of soft pink, cream and light yellow colored hues, the flowers being borne on sturdy stems in a bush of relatively short height and blooming in the mid-season of Spring.

BACKGROUND OF THE NEW PLANT

This variety of peony plant began as a seedling produced by my crossing of Mons. Jules Elie (unpatented) with W. L. Gumm (unpatented), the latter being the pollen parent, in the course of extensive breeding efforts carried on at Arlington Heights, Ill., with the object of developing reliable peonies which have strong stiff stems, are basically weather resistant, and which bloom every year with large showy double blossoms. The present variety was selected by me in 1952 for propagation and test because of the pleasant blend of the pastel colors of its flowers and because of its strong stemmed growth habit which would be of distinct advantage for home garden and landscape use.

Asexual propagation of this plant by root divisions at Arlington Heights, Ill., and under my direction, through many generations, has demonstrated that all of the desirable characteristics of growth habit and flower coloration found in the original seedling are carried by each of the successive generations and are therefore believed to be firmly fixed. Propagation of this new peony plant variety, by root divisions, is now being done under my supervision at production farms in Barrington, Ill., and at Champaign, Ill.

DESCRIPTION OF THE DRAWING

This new variety of peony plant is illustrated by the accompanying photographic drawing, in color, which shows the flower form of the blossom in full bloom. The soft pink color of the print is as nearly true to that of the flower as it is reasonably possible to obtain by conventional professional photographic procedures and the true pink color is intended to be shown by the swatch of painted color affixed to the drawing below the photographic print.

DESCRIPTION OF THE PLANT

The following is a detailed description of my new variety of peony plant with color specifications according to The R.H.S. Colour Chart published by The Royal Horticultural Society of London, England, the observations having been made by me at Arlington Heights, Ill.

THE PLANT

Origin: Seedling.
Parentage:
*Seed Parent.*—Mons. Jules Elie (unpatented).
*Pollen Parent.*—W. L. Gumm (unpatented).
Classification: Paeonia Lactiflora.
Form: Bush.
Shape: Round.
Height: 25 to 28 inches.

Growth: Herbaceous; upright and sturdy with medium strength and stems of about 11/32 to 15/32 inch in diameter.
Foliage: Abundant, with 7 to 8 leaves per stem.
*Leaf Size.*—9 to 11 inches. Shape—Elliptically acute with smooth margins. Aspect—Smooth and glossy. Ribs and Veins—Pronounced on dorsal and ventral sides. Petioles—2 to 2½ inches long. Rachis—¾ to 1 inch in length.
*Leaflets.*— 3 in number. Size—4 to 5 inches in length.
*Color.*—Upper Side—Forest Green. Under Side—Medium Green.

THE BUD

Size: Medium
*Diameter.*—About 17/64 inches
*Depth.*—About 1¼ inches
Form: Ovoid.
Aspect: Smooth.
Opening Rate: Usual and relative to weather.
Sepals: Hooded over bud; curl downwardly as bud opens.
Calyx: Shape—Funnel.
*Size.*—Medium.
*Aspect.*—Smooth.
*Splitting.*—Calyx does not split.
Peduncle: Of average length.

THE FLOWER

Blooming Habit: Plant blooms profusely, once each year in mid-Spring.
Borne: Singly with 2 to 4 axillary buds on each stem.
Size: Medium.
*Diameter.*—Approximately 6 to 7 inches.
*Depth.*—3 inches at crown of the flower.
Shape: Cup shaped, when bloom first opens, changing to bomb shape as bloom matures with the guard petals falling outwardly to allow an inside tuft of petaloids to develop into a round ball shape surrounded by a radially extending collar.
Petalage: Multitudiness, with over 200 petals.
*Arrangement.*—Imbricated, with one or two rows of guard petals.
*Form.*—Spatulate, with notched and slightly ruffled margin.
*Color.*—Outer Petals—Pink—Red Group 49C. Inside Petals—Very pale pink to near white. Reverse Side—Pink—Red Group 49C.
*Texture.*—Soft.
*Appearance.*—Satiny.
Petaloids: 80 to 90 in number.
*Size.*—1¾ to 2 inches long x ⅜ to ½ inch wide.
Fragrance: Slight sweet peony fragrance.
Disease Resistance: From 21 years of observation, this variety appears to be resistant to the common peony diseases.
Persistence: Flower petals fall singularly as bloom reaches final stages of maturity.
Lasting Quality:
*On Plant.*—About 3 weeks.
*As Cut Flower.*—7 to 8 days.

REPRODUCTIVE ORGANS

Stamens: None.
Pistils: 3 to 4 in number, 1 to 1⅛ inch long.
Stigmas: Color—Soft mint-green yellow.

This new peony plant is an early blooming variety, very pleasant to behold because of the outstanding and unique blend of soft pink, cream and yellow hues found in the blossoms. The plant height is relatively short for the size of the flowers, the coloring of which is enhanced by the abundant deep green foliage, and its appearance and growth habit make this plant a good strong stemmed variety for home gradening and landscape use.

I claim:

1. A new and distinct variety of peony plant substantially as herein shown and described, characterized by the blend and combination soft pink and cream colors of its bomb shaped flower form, the relatively short height of the plant growth, and its profuse production of flowers borne on sturdy, stiff stems.

No references cited.

ROBERT E. BAGWILL, Primary Examiner